US00PP20839P2

(12) United States Plant Patent
Morales

(10) Patent No.: US PP20,839 P2
(45) Date of Patent: Mar. 16, 2010

(54) ***AGAPANTHUS* PLANT NAMED 'BLUE MEDUSA'**

(50) Latin Name: *Agapanthus hybrida*
Varietal Denomination: Blue Medusa

(76) Inventor: Manuel Morales, P.O. Box 1296, Royal Oaks, CA (US) 95076

( * ) Notice: Subject to any disclaimer, the term of this patent is extended or adjusted under 35 U.S.C. 154(b) by 0 days.

(21) Appl. No.: 12/283,323

(22) Filed: Sep. 10, 2008

(51) Int. Cl.
*A01H 5/00* (2006.01)

(52) U.S. Cl. ..... Plt./398

(58) Field of Classification Search ..... Plt./398
See application file for complete search history.

*Primary Examiner*—Kent L Bell

(57) ABSTRACT

A new and distinct *Agapanthus* cultivar named 'Blue Medusa' is disclosed, characterized by having distinctive dark violet-blue flower coloration, unusual undulating, darkly colored scapes, with short leaves arranged in irregular whorls. The new variety is an *Agapanthus*, normally produced as an outdoor garden or container plant.

1 Drawing Sheet

Figure 1:
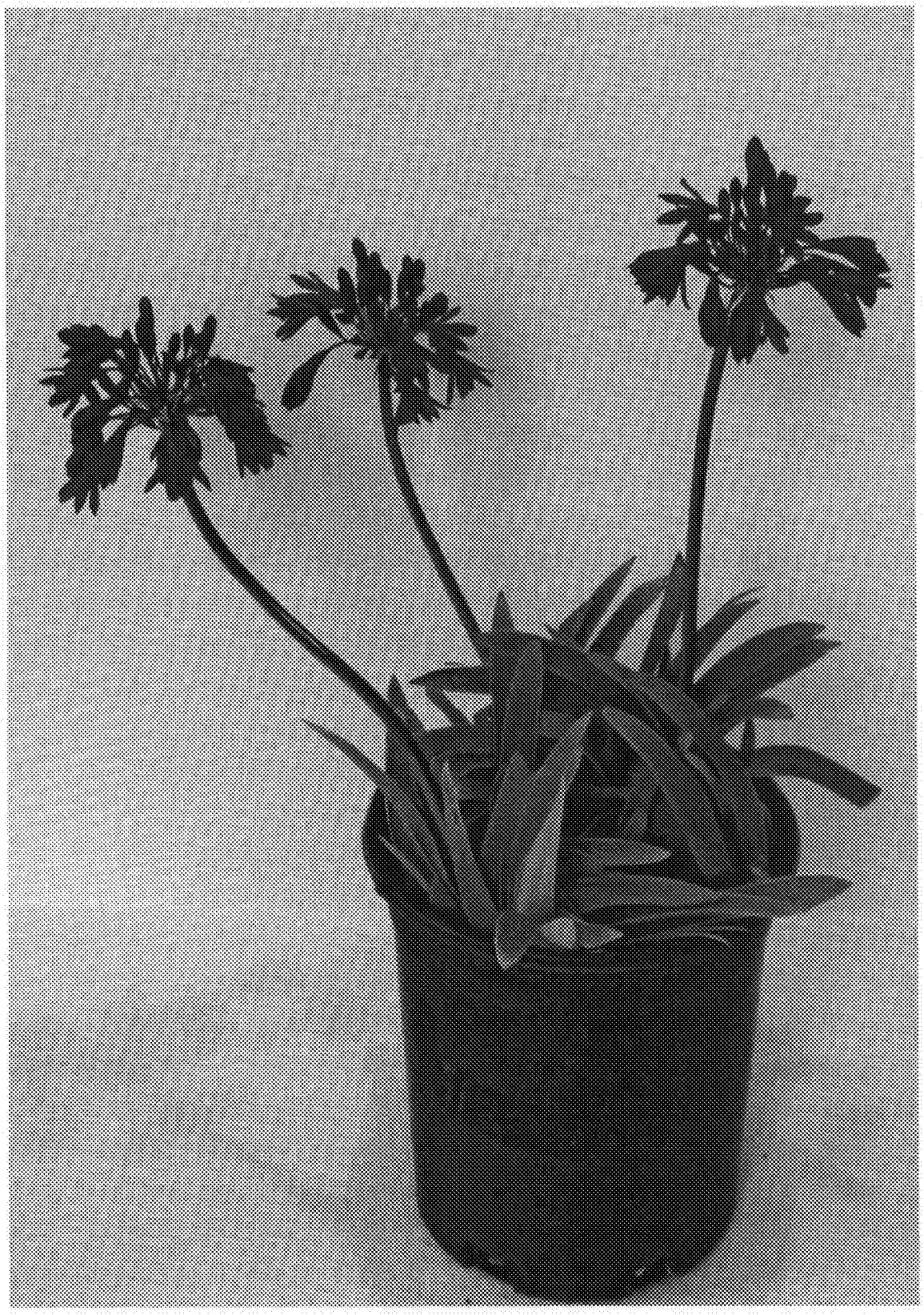

Latin name of the genus and species: *Agapanthus hybrida.*
Variety denomination: 'Blue Medusa'.

BACKGROUND OF THE INVENTION

The new cultivar was discovered as a spontaneous whole plant mutation by the inventor, Manuel Morales. The parent variety is the unpatented, variety *Agapanthus hybrida* 'Storm Cloud.' The new variety was discovered as a naturally occurring, whole plant mutation, May of 2003, by the inventor in a commercial planting of approximately 1000 plants of *Agapanthus hybrida* 'Storm Cloud' an unpatented variety, at a commercial nursery in Monterey, Calif.

Asexual reproduction of the new cultivar 'Blue Medusa' by division was first performed at a commercial nursery in Monterey, Calif. in 2003, and has shown that the unique features of this cultivar are stable and reproduced true to type on successive generations.

SUMMARY OF THE INVENTION

The cultivar 'Blue Medusa' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Blue Medusa'. These characteristics in combination distinguish 'Blue Medusa' as a new and distinct *Agapanthus* cultivar:

1. Distinctive dark violet-blue flower coloration.
2. Unusual undulating scapes.
3. Distinctive dark coloration of scapes.
4. Short leaves, arranged in irregular whorls.

PARENT COMPARISON

Plants of the new cultivar 'Blue Medusa' are similar to plants of the parent variety, *Agapanthus hybrida* 'Storm Cloud' in most horticultural characteristics, however, plants of the new cultivar 'Blue Medusa' have darker scapess, that are much more undulating. Additionally, 'Blue Medusa' produces shorter foliage growing at a broader angle to the center of the plant than the parent variety.

COMMERCIAL COMPARISON

Plants of the new *Agapanthus* is best compared to the parent variety, as it is the most similar commercial *Agapanthus* to 'Blue Medusa.'

BRIEF DESCRIPTION OF THE PHOTOGRAPH

The accompanying photograph in FIG. 1 illustrates in full color a typical plant of 'Blue Medusa' grown outdoors in Monterey, Calif. during Spring and Summer, in a 1 gallon nursery pot. Age of the plant photographed is approximately 7 months from a vegetative division. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Blue Medusa' plants grown outdoors in Monterey, Calif. The growing temperature ranged from 15° C. to 35° C. during the day and approximately 10° C. to 25° C. at night. The plants were not grown with any kind of shade protection and subject to outdoor, high light conditions. Measurements and numerical values represent averages of typical plant types. No growth retardants were used.

Botanical classification: *Agapanthus hybrida* cultivar 'Blue Medusa.'

PROPAGATION

Time to initiate roots: About 30 days at approximately 20° C.

Root description: Typical *Agapanthus* root, freely branching and near RHS Greyed-Yellow 162D in color.

Propagation method: Vegetative divisions or tissue culture.

PLANT

Growth habit: Upright flowering plant. Irregularly whorled strap-like leaves emerge basally.
Age of plant described: Approximately 7 months.
Container size: 1 gallon.
Height: Approximately 15 cm to top of highest leaf. Approximately 28 cm to top of highest inflorescence.
Plant spread: Approximately 22 cm.
Growth rate: Moderate.
Branching characteristics: Non-branching, forms basal clumps.

FOLIAGE

Leaf:
*Arrangement.*—Basal, irregular whorls.
*Attachment.*—Sessile.
*Average length.*—Approximately 9 cm.
*Average width.*—Approximately 1.5 cm.
*Shape of blade.*—Linear.
*Apex.*—Acute.
*Base.*—Cuneate.
*Margin.*—Entire.
*Texture of top surface.*—Slightly ridged, glabrous.
*Texture of bottom surface.*—Very slightly ridged, glabrous.
*Quantity of leaves per plant.*—Approximately 30.
*Color.*—Young foliage upper side: Near RHS Green 138A. Young foliage under side: Near RHS Green 138A. Mature foliage upper side: Near RHS Green 138A. Mature foliage under side: Near RHS Green 138A.
*Venation.*—Type: Linear. Venation color upper side: Near RHS Green 138A. Venation color under side: Near RHS Green 138A.

FLOWER

Natural flowering season: Naturally flowers summer through late Autumn.
Inflorescence type and habit: Scapose with single campanulate flower; flowers arranged in umbels on undulating scapes.
Rate of flower opening: Approximately 8 days from bud to fully opened flower.
Flower longevity on plant: At least 18 days, after fully opened. Self cleaning.
Quantity of flowers per inflorescence: Plants have approximately 15 open flowers at all times and approximately 15 buds.
Quantity of flowering stems: Plants have typically 5 flowering stems per plant.
Umbel inflorescence size:
*Height.*—Approximately 11 cm.
*Width.*—Approximately 5.2 cm.
Tepals:
*Arrangement.*—Apetalous, single, campanulate flowers composed of 5 basally fused tepals, shaped into a flared trumpet.
*Size.*—Length: Approximately 2.5 cm. Width: Approximately 1.8 cm at widest point. Lobe length: Approximately 1.1 cm. Lobe width: 0.3 cm.
*Margin.*—Entire.
*Shape.*—Lanceolate, strongly concave while maturing, opening to become reflexed back.
*Apex.*—Obtuse, concave.
*Texture.*—Glabrous.
Color:
*Tepals.*—When opening: Outer surface: Near RHS Violet-Blue 93A. Inner surface: Near RHS Violet-Blue 93 B with steaks near RHS Violet-Blue 93A.
*Fully opened.*—Outer surface: Near RHS Violet N88A. Inner surface: Near RHS Violet-Blue N89C with steaks near RHS Violet-Blue 93D. Color Changes when Aging: No color change.
Bud:
*Shape.*—Ovate to Lanceolate.
*Length.*—Approximately 2.1 cm.
*Diameter.*—Approximately 0.4 cm.
*Color.*—Near RHS Violet-Blue N92B.
Sepals: Not present.
Pedicels:
*Length.*—Approximately 2.4 cm.
*Width.*—Approximately 0.1 cm.
*Aspect.*—Undulating.
*Color.*—Near RHS Green 137B.
Scape:
*Length.*—Approximately 17.5 cm.
*Width.*—Approximately 0.6 cm.
*Angle.*—Upright from center of plant, then, highly undulating.
*Strength.*—Very strong.
*Color.*—Near RHS Green 138A with deep blush of Violet-Blue N92A.
Fragrance: None.

REPRODUCTIVE ORGANS

Stamens:
*Number.*—Average 6.
*Filament length.*—Approximately 1.4 cm.
*Filament color.*—Near RHS 91A to 91B.
*Anther length.*—0.2 cm.
*Anther color.*—Near RHS Violet-Blue N92B.
*Anther shape.*—Oblong.
*Pollen.*—None observed.
Pistil:
*Number.*—1.
*Length.*—Approximately 2.4 cm.
*Style color.*—Near RHS 91B.
*Stigma.*—Shape: Linear. Color: Near RHS Violet-Blue 92A.
*Ovary color.*—Near RHS Yellow-Green 150B.

OTHER CHARACTERISTICS

Seeds and fruits: Not observed to date.
Disease/pest resistance: Neither resistance nor susceptibility to pathogens and pests common to *Agapanthus* have been observed.
Temperature tolerance: Tolerates temperatures from approximately −1° C. to 40° C.

What is claimed is:

1. A new and distinct cultivar of *Agapanthus* plant named 'Blue Medusa' as herein illustrated and described.

* * * * *